United States Patent
Warnock

(10) Patent No.: US 9,549,743 B2
(45) Date of Patent: Jan. 24, 2017

(54) BONE GRAFT HARVESTING DEVICE AND METHOD OF USE

(71) Applicant: Innospan Enterprises, Inc., Draper, UT (US)

(72) Inventor: Steven H. Warnock, Salt Lake City, UT (US)

( * ) Notice: Subject to any disclaimer, the term of this patent is extended or adjusted under 35 U.S.C. 154(b) by 327 days.

(21) Appl. No.: 14/276,806

(22) Filed: May 13, 2014

(65) Prior Publication Data

US 2014/0343554 A1    Nov. 20, 2014

Related U.S. Application Data

(60) Provisional application No. 61/823,301, filed on May 14, 2013.

(51) Int. Cl.
*A61B 17/16* (2006.01)
*A61B 17/17* (2006.01)
*A61B 17/88* (2006.01)

(52) U.S. Cl.
CPC ....... *A61B 17/1635* (2013.01); *A61B 17/1615* (2013.01); *A61B 17/1662* (2013.01); *A61B 17/1739* (2013.01); *A61B 17/8866* (2013.01)

(58) Field of Classification Search
CPC .... A61B 17/1635; A61B 17/17; A61B 10/025
See application file for complete search history.

(56) References Cited

U.S. PATENT DOCUMENTS

| | | |
|---|---|---|
| 5,556,399 A | 9/1996 | Huebner |
| 5,954,671 A | 9/1999 | O'Neill |
| 7,780,668 B2 * | 8/2010 | Steiner .................. A61F 2/4644 269/87 |
| 7,901,404 B2 | 3/2011 | Reay-Young |
| 8,043,291 B2 | 10/2011 | Accordino |
| 2005/0177159 A1 | 8/2005 | Guzman et al. |

FOREIGN PATENT DOCUMENTS

WO    2005069924 A2    8/2005

OTHER PUBLICATIONS

International Search Report and Written Opinion of the International Searching Authority from related PCT Application No. PCT/US14/37912, dated Oct. 10, 2014.

* cited by examiner

*Primary Examiner* — Andrew Yang
(74) *Attorney, Agent, or Firm* — Sarah Matthews; Randall Bateman

(57) ABSTRACT

A device is provided to harvest bone grafts. The device generally consists of two pieces: an auger-type drill bit and a guide. The guide may have arms, etc., to keep the guide in place along a bone, and also may have a pivotable drill guide for the drill bit to be inserted. The auger drill bit may include a shoulder that acts as a depth guide to prevent the drill from extending too deep into bone. The device may be used to make multiple passes through a bone using only one drill hole. A method for harvesting bone graft is also provided.

19 Claims, 8 Drawing Sheets

BONE GRAFT HARVESTING DEVICE AND METHOD OF USE

BACKGROUND OF THE INVENTION

1. The Field of the Invention

The present invention relates generally to a drill and method for extracting bone grafts. More specifically, the present invention relates to removing bone graft material from a patient using a combination drill bit and guide.

2. State of the Art

In the course of a variety of surgeries, it becomes necessary to graft bone from one part of the body to another in an effort to strengthen bones that have had operations. For example, bone grafting is very common in orthopedic surgery, neuro/spine surgery, and plastic surgery. Several bone graft products are commercially available and usually depend on bone harvested from cadaver donors (allograft bone). However, processing of cadaver bone may have deleterious effects on the biological properties of the bone products. Allografts are only osteoconductive, and they involve considerable cost, pose the risk of disease transmission, and are objectionable to certain religious groups.

Autologous bone grafts are harvested directly from the patient and are considered to be the "gold standard," because they are inherently biocompatible, osteoconductive, osteoinductive, and osteogenic. Harvesting autologous bone is usually carried out by taking bone from a part of the patient's body other than the surgical site. This results in additional surgical time and the additional surgical harvest has its own attendant risk of complications, such as donor site pain and morbidity. The major disadvantage of autograft bone is that it requires harvesting of bone from a separate donor site which prolongs surgical time and creates donor site morbidity. Many patients complain that the pain associated with the donor site is greater than that of the primary operative site. The iliac crest of the pelvis is a common donor site, and one current method for harvesting bone from the iliac crest includes using a trephine device to take a core sample of bone.

It is advantageous to have a technique for harvesting bone from the iliac crest of the pelvis (a very common donor site) in a way that limits donor site pain, speeds the harvesting process, and provides adequate bone volume for a variety of surgical needs.

SUMMARY OF THE INVENTION

According to one aspect of the present disclosure, a surgical tool and method for harvesting bone is provided. The tool may comprise an auger-type drill bit and a guide for the drill bit. The guide may allow a surgeon to make not just one pass through the iliac to harvest bone, but multiple passes through the iliac from a single incision to obtain the adequate bone volume necessary.

According to one configuration, the auger-type drill bit may include a generally cylindrical wall forming an elongate hollow cylindrical shaft with a helical blade at the distal end. The helical blade may have a cutting edge at the tip to cut bone.

According to another aspect of the present disclosure, the auger drill bit may include a void in the elongate hollow cylindrical shaft defined by the cylindrical wall from which bone may be removed.

According to another aspect of the present disclosure, the guide may be comprised of two elongate arms configured to be placed on either side of the iliac bone from which bone material is to be harvested.

According to another aspect of the present disclosure, the guide may include a drill guide pivotally mounted thereon, with the drill guide being configured to receive the auger drill bit. The drill guide may be configured to pivot only in the plane of a bone, such as the iliac bone.

According to another aspect of the present disclosure, the auger drill bit may include a shoulder near the proximal end. The shoulder may have a diameter larger than the diameter of the drill guide; the shoulder may thus act as a depth guide to prevent the auger drill bit from drilling too deep into a bone. Auger drill bits of various lengths and diameters may be provided.

According to another aspect of the present disclosure, the two elongate arms on the guide may be spaced a distance apart, and configured to be adjustable such that the space between the two arms can be increased or decreased according to the particular patient's needs. According to yet another aspect of the present disclosure, guides with arms at various widths may be provided.

According to another aspect of the present disclosure, the drill guide may be fitted with a handle for use by the surgeon to help stabilize the apparatus against the bone during drilling.

According to another aspect of the present disclosure, the drill guide may be provided with a bone clamping mechanism. The bone clamping mechanism may include 2-3 elongate arms and a handle to adjust the elongate arms to apply inward pressure to hold or secure the drill guide to a bone. According to another aspect, a latching mechanism may be provided to secure the bone clamping mechanism in place.

According to another aspect of the present disclosure, a method is provided wherein a surgeon may make a single incision, place the guide as provided herein, and place the auger drill bit through the drill guide to remove bone. The surgeon may adjust the pivotable drill guide to make multiple passes through the bone within the same incision site.

These and other aspects of the present invention are realized in a bone graft harvesting device and method of use as shown and described in the following figures and related description. It will be appreciated that various embodiments of the invention may not include each aspect set forth above and aspects discussed above shall not be read into the claims unless specifically described therein.

BRIEF DESCRIPTION OF THE DRAWINGS

Various embodiments of the present disclosure are shown and described in reference to the numbered drawings wherein.

Figure 1:
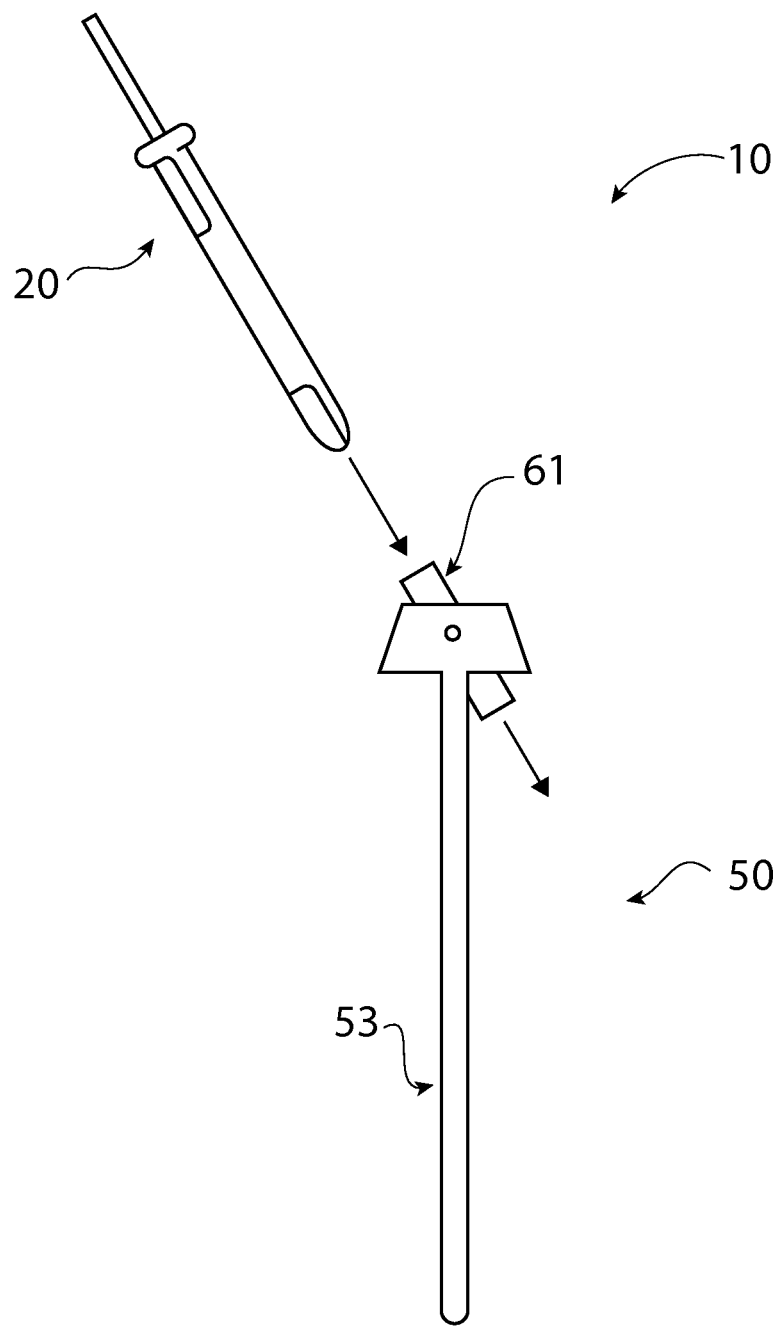
FIG. 1 shows a side view of an exemplary configuration of bone harvesting device as disclosed herein.

It will be appreciated that the drawings are illustrative and not limiting of the scope of the invention which is defined by the appended claims. The embodiments shown accomplish various aspects and objects of the invention. It is appreciated that it is not possible to clearly show each element and aspect of the invention in a single figure, and as such, multiple figures are presented to separately illustrate the various details of the invention in greater clarity. Similarly, not every embodiment need accomplish all advantages of the present invention.

DETAILED DESCRIPTION

The invention and accompanying drawings will now be discussed in reference to the numerals provided therein so as to enable one skilled in the art to practice the present invention. The skilled artisan will understand, however, that the methods described below can be practiced without employing these specific details, or that they can be used for purposes other than those described herein. Indeed, they can be modified and can be used in conjunction with products and techniques known to those of skill in the art in light of the present disclosure. The drawings and descriptions are intended to be exemplary of various aspects of the invention and are not intended to narrow the scope of the appended claims. Furthermore, it will be appreciated that the drawings may show aspects of the invention in isolation and the elements in one figure may be used in conjunction with elements shown in other figures.

Reference in the specification to "one embodiment," "one configuration," "an embodiment," or "a configuration" means that a particular feature, structure, or characteristic described in connection with the configuration may be included in at least one configuration, etc. The appearances of the phrase "in one embodiment" in various places may not necessarily limit the inclusion of a particular element of the invention to a single embodiment, rather the element may be included in other or all embodiments discussed herein.

Furthermore, the described features, structures, or characteristics of configurations of the present disclosure may be combined in any suitable manner in one or more configurations. In the following description, numerous specific details are provided, such as examples of products or manufacturing techniques that may be used, to provide a thorough understanding of configurations of the invention. One skilled in the relevant art will recognize, however, that configurations discussed in the disclosure may be practiced without one or more of the specific details, or with other methods, components, materials, and so forth. In other instances, well-known structures, materials, or operations are not shown or described in detail to avoid obscuring aspects of the invention.

Before the present invention is disclosed and described in detail, it should be understood that the present invention is not limited to any particular structures, process steps, or materials discussed or disclosed herein, but is extended to include equivalents thereof as would be recognized by those of ordinarily skill in the relevant art. More specifically, the invention is defined by the terms set forth in the claims. It should also be understood that terminology contained herein is used for the purpose of describing particular aspects of the invention only and is not intended to limit the invention to the aspects or configurations shown unless expressly indicated as such. Likewise, the discussion of any particular aspect of the invention is not to be understood as a requirement that such aspect is required to be present apart from an express inclusion of the aspect in the claims.

It should also be noted that, as used in this specification and the appended claims, singular forms such as "a," "an," and "the" may include the plural unless the context clearly dictates otherwise. Thus, for example, reference to "a spring" may include one or more of such springs, and reference to "the layer" may include reference to one or more of such layers.

As used herein, the term "substantially" refers to the complete or nearly complete extent or degree of an action, characteristic, property, state, structure, item, or result to function as indicated. For example, an object that is "substantially" enclosed would mean that the object is either completely enclosed or nearly completely enclosed. The exact allowable degree of deviation from absolute completeness may in some cases depend on the specific context, such that enclosing the nearly all of the length of a lumen would be substantially enclosed, even if the distal end of the structure enclosing the lumen had a slit or channel formed along a portion thereof. The use of "substantially" is equally applicable when used in a negative connotation to refer to the complete or near complete lack of an action, characteristic, property, state, structure, item, or result. For example, structure which is "substantially free of" a bottom would either completely lack a bottom or so nearly completely lack a bottom that the effect would be effectively the same as if it completely lacked a bottom.

As used herein, the term "about" is used to provide flexibility to a numerical range endpoint by providing that a given value may be "a little above" or "a little below" the endpoint while still accomplishing the function associated with the range.

As used herein, a plurality of items, structural elements, compositional elements, and/or materials may be presented in a common list for convenience. However, these lists should be construed as though each member of the list is individually identified as a separate and unique member.

Concentrations, amounts, proportions and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually. This same principle applies to ranges reciting only one numerical value as a minimum or a maximum. Furthermore, such an interpretation should apply regardless of the breadth of the range or the characteristics being described.

Distal and proximal, as used herein, are from the perspective of the person using the bone harvesting device. Thus, proximal means nearer to the user and distal means farther from the person drilling. The drill described herein thus has a distal end which performs the bone cutting and a proximal end where the bone may be collected, as described below.

Turning now to FIG. 1, a side view of a one possible configuration of a bone graft harvesting device disclosed herein is shown. The device, generally indicated at 10, maybe comprised of two parts: an auger-type drill bit, generally indicated at 20, and a guide, generally indicated at 50, to assist the surgeon in making multiple passes within a bone. The guide ay include two elongate arms 53 to assist in keeping the guide in place along the bone, and may also include a pivotable drill guide 61 to keep the auger drill bit 20 cutting in the plane of the bone.

Turning now to FIG. 2, there is shown a detailed side view of one possible configuration of an auger drill bit, generally indicated at 20. The auger drill bit 20 may include a body forming an outer wall defining a hollow, generally cylindrical shaft portion 22. The cylindrical shaft portion 22 has a distal end 28 and a proximal end 31. The auger drill bit 20 may also include a helical cutting edge 37 at the distal end 28. The cutting edge 37 at the distal end 28 may engage the bone and cut the bone graft material. The bone graft material may then be propelled up inside the hollow shaft portion 22 by the pushing of more bone material into the distal end 28.

Figure 2A:
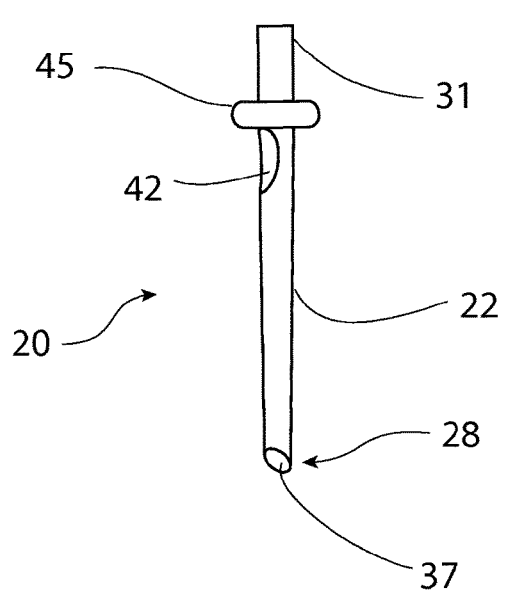
FIG. 2A shows a side view of the auger drill bit of the bone harvesting device disclosed herein.
Figure 2B:
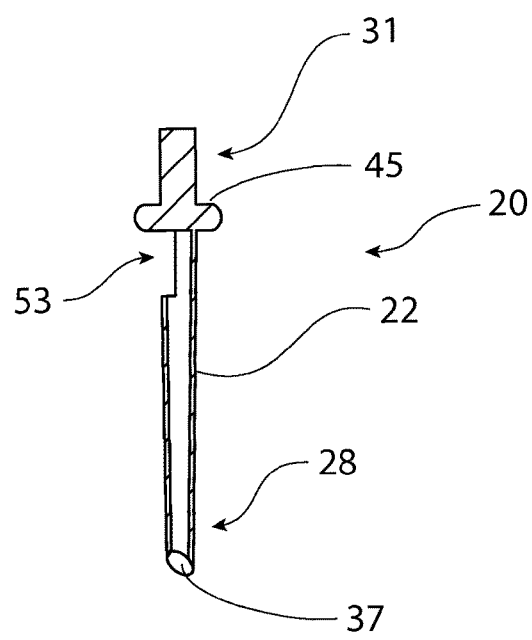
FIG. 2B shows a cross-section view of the auger drill bit of FIG. 2A.

FIG. 2B shows a cross-sectional view of FIG. 2A, with the helical cutting edge 37 visible through the cylindrical shaft portion 22. The shaft portion 22 may be provided with a void 42 near the proximal end 31. This void may be used to remove portions of bone cut by the helical cutting edge 37. As the bone is cut, the rotating helical cutting edge 37 may act to propel or move the drilled bone proximally within the elongate cylindrical hollow shaft 22; the rotation of the helical cutting edge 37 causes the bone material to move proximally out of the hole being drilled. The void 42 disposed at the proximal end 31 of the shaft portion 22 may be used to remove the morselized bone. In some configurations, the proximal end 31 may include a collecting cup such that the morselized bone exits the void 42 and is collected in the collecting cup. As the auger drill bit 20 is moved deeper inwardly through the donor bone, continuous cutting action occurs and morselized bone can then be removed from the void 42 at the proximal end 31 of the shaft 22. This morselized bone can then be used to build up bone in other areas to which it is transplanted.

The shaft portion 22 may also be provided with a shoulder 45 near the proximal end 31. As described below, this shoulder 45 may act as a depth guide, to prevent the hole being drilled in the bone from going too deep into the bone. The shoulder portion 45 may extend radially outward such that it has a diameter larger than the diameter of the drill guide 61 (FIG. 1). Thus, the auger drill bit 20 cannot be extended through the drill guide 61 past the shoulder 45. The appropriate depth of the hole into the bone may vary from patient to patient, and thus auger drill bits 20 of different lengths with different shoulder positions may be manufactured. Surgeons may select the auger drill bit 20 of the appropriate length for the patient.

Figure 3:
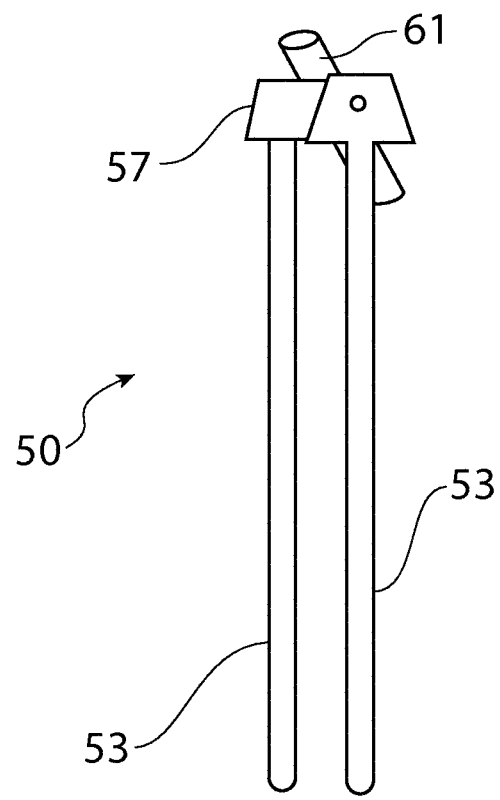
FIG. 3 shows a perspective view of the guide of the bone harvesting device disclosed herein.

Turning now to FIG. 3, there is shown a perspective view of one possible configuration of the guide, generally indicated at 50. The guide 50 may include two elongate arms 53, a head portion 57, and a drill guide 61. The two elongate arms 53 may be connected through the head portion 57, and extend distally from the head portion 57. The two arms 53 may be configured such that one arm is disposed on one side of a bone (e.g., the iliac bone) to be drilled, and the other arm is disposed on an opposing side of the bone to be drilled. Thus, the two elongate arms 53 can form a bone guide, and may keep the guide 50 in contact with, and properly aligned with respect to, the bone from which bone material is to be removed.

Figure 4:
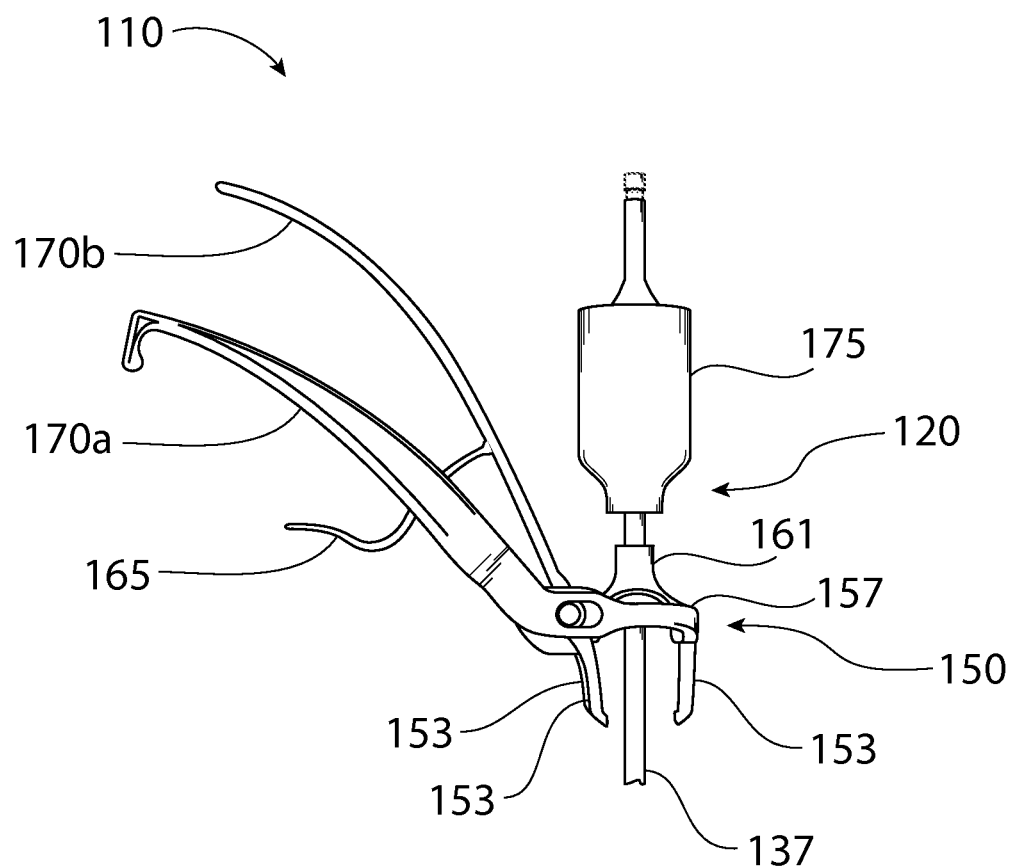
FIG. 4 shows a side view of another exemplary configuration for a bone harvesting device as disclosed herein.
Figure 5:
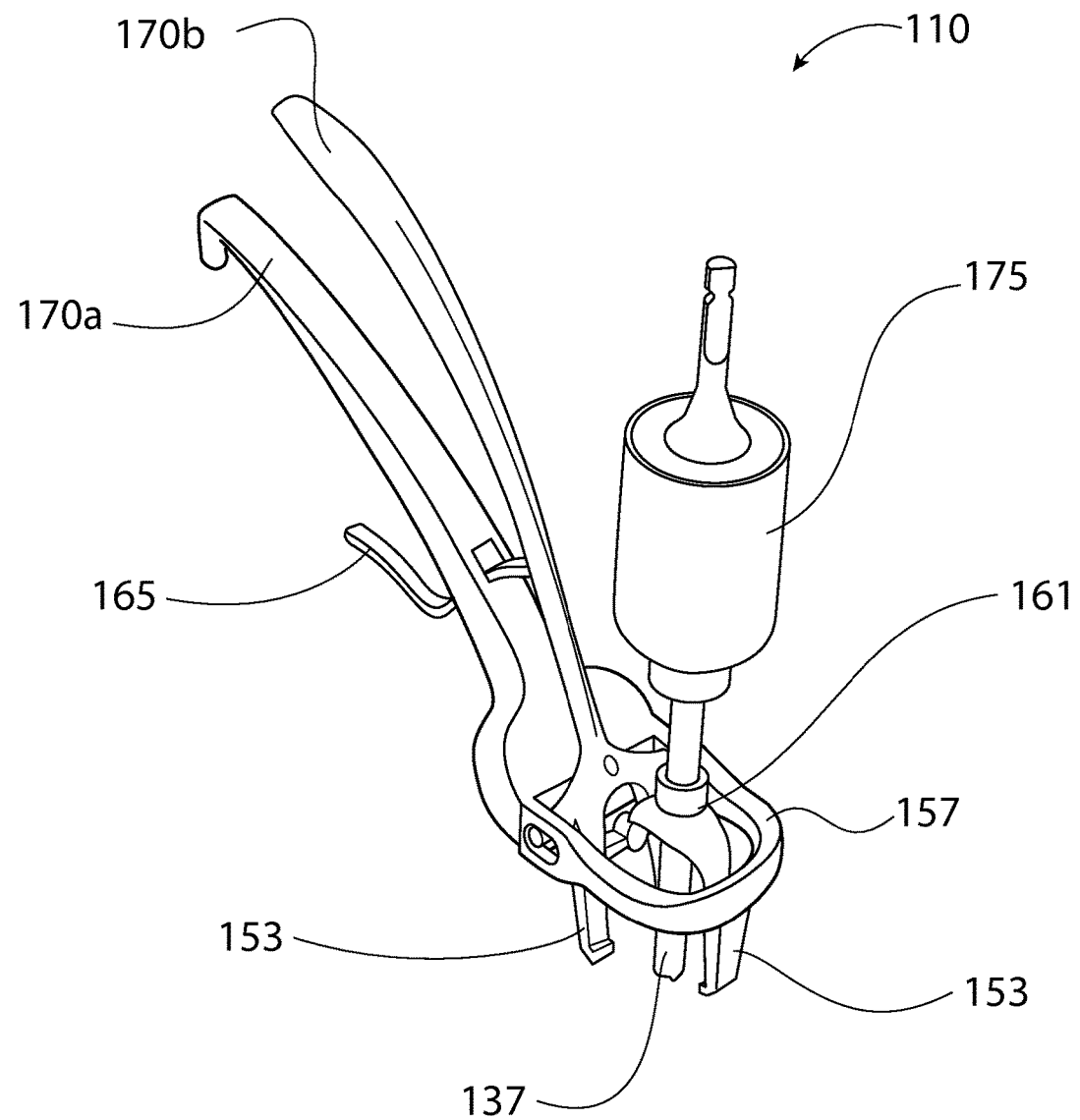
FIG. 5 shows a perspective view of the device shown in FIG. 4.
Figure 6:
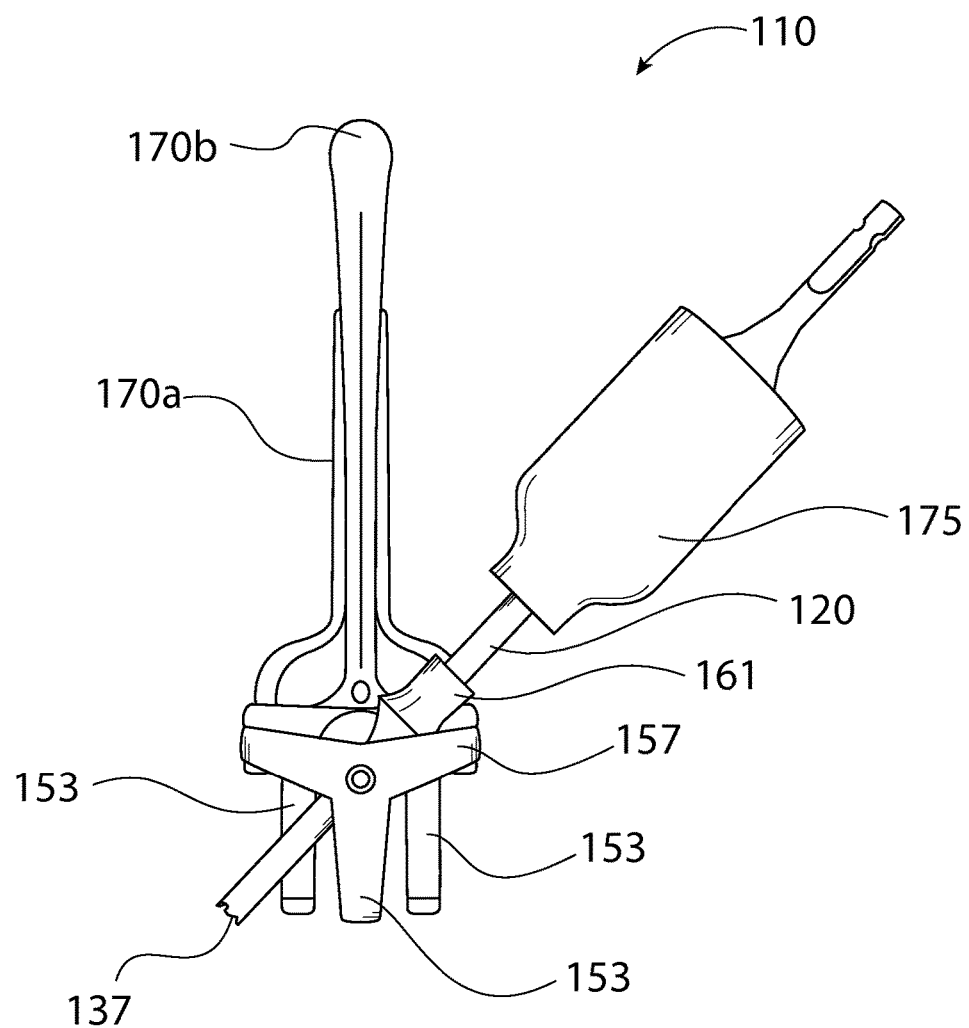
FIG. 6 shows a front view of the device shown in FIG. 4 with the drill guide and auger shown in a pivoted position.

There may be various other means used to keep the guide 50 in contact with, and properly aligned with respect to, the bone from which bone material is to be removed. For example, FIGS. 4-6 show another possible configuration of a device as disclosed herein that utilizes a bone clamping mechanism to keep the guide in contact with the bone from which material is to be removed. Turning to FIG. 4, a device is generally indicated at 110, the device including a drill guide 150 with an auger 120. The auger may include a cutting edge 137, as well as a collecting cup 175 for collecting morselized bone.

According to this configuration, the guide 150 is provided with a bone clamping mechanism 155 to assist in keeping the guide 150 in its proper place. The bone clamping mechanism 155 may include 2-3 elongate arms 153, as well as a handle 170b to adjust the elongate arms 153. A handle 170a may also be provided. The handle 170a may be used by a surgeon to help stabilize the apparatus against the bone during drilling. A latching mechanism 165 may be used to latch the handle portion 170b in place relative to the handle 170a.

The bone clamping mechanism 155 may be used to apply inward pressure on a bone through the elongate arms 153 to hold or secure the drill guide 150 to a bone. As the handle 170b is pressed downwardly by a surgeon, the handle 170b acts as a lever to move one or more of the elongate arms 153 inwardly to apply pressure against a bone from which material is to be removed. The latching mechanism 165 may be configured to be secured in place by the surgeon once the bone clamping mechanism 155 is exerting the appropriate amount of inward pressure.

FIG. 5 shows a perspective view of the device shown in FIG. 4, and FIG. 6 shows a front view of the device shown in FIG. 4 with the drill guide and auger shown in a pivoted position. The drill guide 161 may be configured to be pivotable in a single plane. In one configuration, the bone to be removed is bone from the iliac crest. Thus, the two or more elongate arms 153 would be placed on either side of the patient's iliac crest. The surgeon may then press downwardly on the handle portion 170b (moving the handle portion 170b closer to the handle 170a) to move one or more of the elongate arms 153 inwardly such that the inward pressure on the bone holds the device in place. The surgeon may then secure the handle portion 170b in place relative to the handle 170a with the latching mechanism 155.

Figure 7:
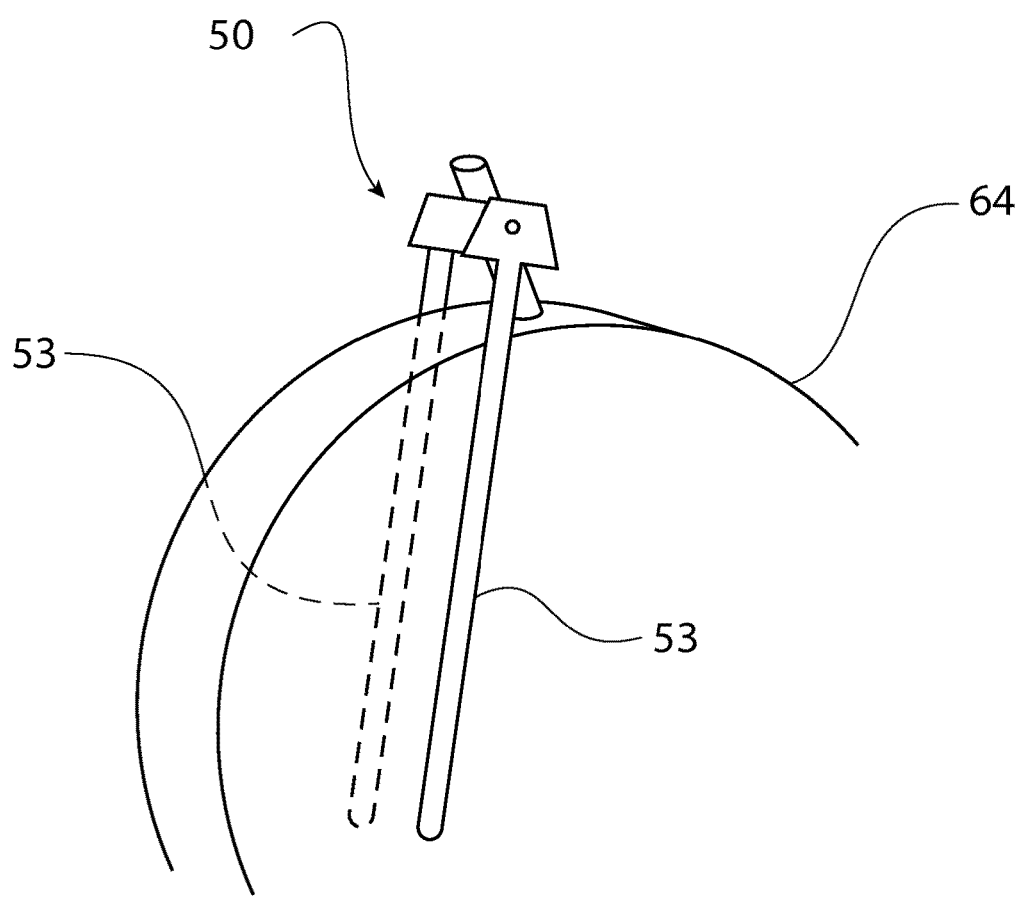
FIG. 7 shows a perspective view of the guide of FIG. 3 as it may be placed on an iliac crest bone.

In another configuration, the bone to be removed is bone from the iliac crest. Thus, according to this exemplary configuration, the two elongate arms 53 would be placed on either side of the patient's iliac crest. Because the width of the iliac crest can vary from patient to patient, the guide 50 may be provided with an adjustable head portion 57 so that elongate arms 53 that may be adjusted to various widths. According to another configuration, multiple guides may be provided with elongate arms 53 at various widths. Thus, the surgeon may select a guide 50 with arms of the appropriate width, or may adjust the width of the arms 53 for the particular patient. FIG. 7 shows a perspective view of the guide 50 on the iliac crest 64 of a patient, with one elongate arm 53 on either side of the iliac crest 64.

At the head portion 57 of the guide 50, a drill guide 61 may be pivotally attached. The drill guide may include a hollow cylinder, or a ring or the like, with the drill guide having a diameter configured to receive the auger drill bit 20. The drill guide 61 may be pivotable in the plane of the bone. The plane of the bone may be the plane that passes through the longest axis of the bone. This pivotable drill guide 61 may make it possible for a surgeon to make multiple passes through the bone and use only a single incision. For example, a surgeon may make a single incision, insert the guide, place the drill guide at a particular angle, and remove bone. The surgeon may then place the drill guide 61 at a second angle by simply pivoting the drill guide 61 to the second angle (with no need to make a new, possibly painful incision for the patient) and then remove bone at the second angle.

Figure 8:
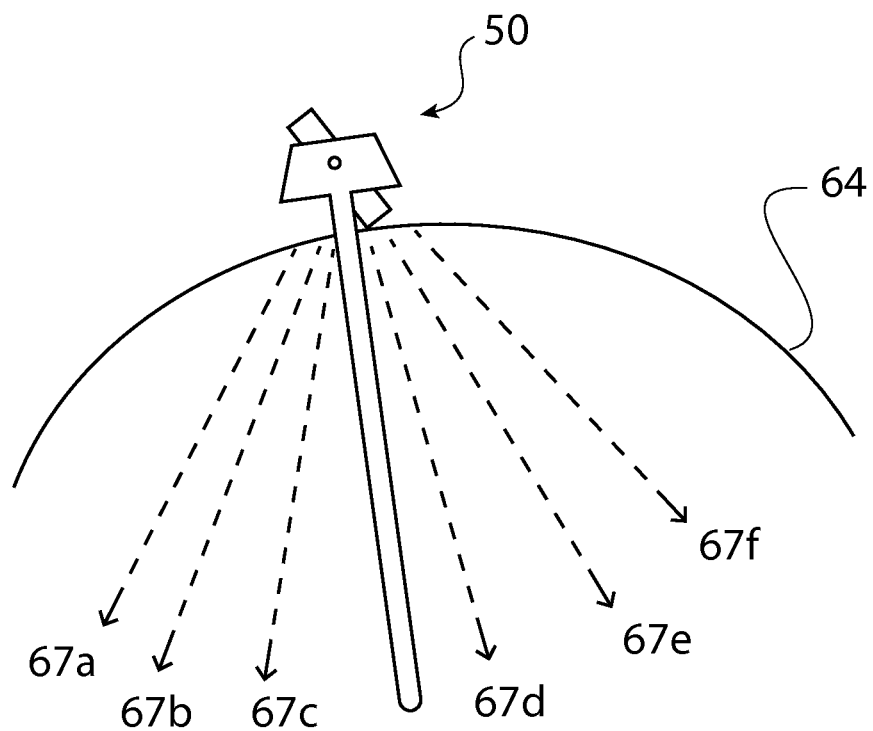
FIG. 8 shows a partial cut-away view of the guide of the bone harvesting device as disclosed herein with potential paths for the auger drill bit to remove bone.

FIG. 8 shows a front view of the guide 50 placed on the iliac crest 64 of a patient. The dashed arrows 67*a*-67*f* show possible exemplary paths the auger drill bit could take through the bone in removing portions of bone. Thus, a surgeon may make multiple passes through the bone to remove bone portions using a single incision entry point.

According to one possible method, the device may be used to harvest bone from the iliac crest. A surgeon may make an incision over the iliac crest, and then carry the dissection down to the surface of the bone. The surgeon may then place the guide 50, with the two arms 53 positioned on either side of the iliac crest, and push the guide 50 down so the guide 50 is secure against the iliac crest and the arms 53 are positioned in the inside and outside of the iliac bone. The surgeon may then place the auger drill bit 20 in the drill guide 61, and drill the auger drill bit 20 into the medullary space. The helical cutting edge 37 cuts the bone, pushing it proximally towards the void 42 where the bone may be extracted. The drill guide 61 may prevent the auger drill bit 20 from being directed outside the plane of the bone, and the shoulder 45 on the auger drill bit 20 may prevent the auger drill bit 20 from going too deep within the bone.

The drill guide 50 may be configured to only rotate in only one axis, parallel to the orientation of the iliac bone, so that bone can be harvested from the medullary space in a fan-like configuration. After the surgeon has made one pass through the bone, the drill guide may be pivoted and the auger drill bit may again be passed through the bone. The steps of pivoting the guide and removing bone through the auger drill bit may be repeated as the surgeon deems necessary for the particular patient. The result is a relatively quick and precise harvesting of medullary bone through a single drill hole.

A bone graft harvesting device as disclosed herein may include an auger drill bit having an elongate hollow cylindrical shaft section having a distal end and a proximal end and a long axis extending therebetween; the distal end including a helical cutting edge; and a guide having a head portion including a drill guide pivotally mounted on the head portion. The auger drill bit may be configured to be inserted into the drill guide.

The bone graft harvesting device may also include a void for removing bone near the proximal end of the elongate cylindrical shaft. The drill guide may be configured to pivot in only one plane. The elongate hollow cylindrical shaft may further comprise a shoulder near the proximal end. The shoulder may extend radially outward such that the shoulder has a diameter, the diameter of the shoulder being greater than the diameter of the drill guide.

The guide of the bone graft harvesting device may include at least two arms extending distally from the head portion. The two arms may be spaced a distance apart, and the two arms may be configured to be adjustable such that the distance may be increased or decreased. The two arms may be configured to engage an iliac crest bone, and may be elongate. The guide may include a handle attached to the head portion. The device may also include bone clamping mechanism comprised of the at least two arms and a handle portion connected to at least one of the at least two arms and the head portion.

A device for harvesting bone from an iliac crest is described herein, and the device may include: an auger drill bit, the auger drill bit having an elongate cylindrical wall and a distal end, the distal end including a helical screw blade; and a guide configured to receive the auger drill bit, the guide having a head portion with at least two arms configured to engage the iliac crest and a pivotable drill guide.

The device may further include an opening in the elongate cylindrical wall. The pivotable drill guide may be defined by a cylindrical wall defining a hollow having a diameter.

The auger drill bit may further include a depth guide, the depth guide including a shoulder having a diameter, the diameter of the shoulder being larger than the diameter of the pivotable drill guide. The pivotable drill guide may only pivot in one plane.

A method for harvesting bone is also disclosed, the method including: disposing a guide along a bone, the guide having a drill guide pivotally connected thereto; inserting an auger drill bit into the drill guide; and drilling into the bone at a first angle. The method may further include the steps of removing the auger drill bit from the drill guide; pivoting the drill guide; inserting the auger drill bit into the drill guide; and drilling into the bone at a second angle.

The auger drill bit may include a helical cutting edge at the distal end, and an elongate cylindrical hollow shaft; and wherein the guide may include a head portion with at least two arms configured to engage the iliac crest and a pivotable drill guide.

The step of disposing a guide along a bone may include pressing the two arms of the guide down such that the two arms are positioned on the inside and outside of the iliac bone. The elongate cylindrical hollow shaft may include a distal end and a proximal end, the proximal end having a void; and the method may further include the step of collecting the drilled bone through the void. 22. The method may also include the step of disposing a guide along a bone by clamping the guide in place on the bone.

There is thus disclosed an improved bone graft harvesting device and method. It will be appreciated that numerous changes may be made to the present invention without departing from the scope of the claims.

What is claimed is:
1. A bone graft harvesting device, including:
an auger drill bit having an elongate hollow cylindrical shaft section having a distal end and a proximal end and a long axis extending therebetween; the distal end including a helical cutting edge and the proximal end including a void for removing bone;
a guide having a head portion including a drill guide pivotally mounted on the head portion;
wherein the auger drill bit is configured to be inserted into the drill guide.
2. The bone graft harvesting device of claim 1, wherein the drill guide is configured to pivot in only one plane.
3. The bone graft harvesting device of claim 1, wherein the elongate hollow cylindrical shaft section further comprises a shoulder near the proximal end.
4. The bone graft harvesting device of claim 3, wherein the drill guide has a diameter, and wherein the shoulder extends radially outward such that the shoulder has a diameter, the diameter of the shoulder being greater than the diameter of the drill guide.

5. The bone graft harvesting device of claim 1, wherein the guide includes at least two arms extending distally from the head portion.

6. The bone graft harvesting device of claim 5, wherein the at least two arms are spaced a distance apart, and wherein the at least two arms are configured to be adjustable such that the distance may be increased or decreased.

7. The bone graft harvesting device of claim 5, further including a bone clamping mechanism comprised of the at least two arms and a handle portion connected to at least one of the at least two arms and the head portion.

8. The bone graft harvesting device of claim 5, wherein the at least two arms are elongate.

9. The bone graft harvesting device of claim 1, wherein the guide includes a handle attached to the head portion.

10. A device for harvesting bone from an iliac crest, the device including:
   an auger drill bit, the auger drill bit having an elongate cylindrical wall and a distal end, the distal end including a helical screw blade;
   a guide configured to receive the auger drill bit, the guide having a head portion with at least two arms configured to engage the iliac crest and a pivotable drill guide; and
   wherein the pivotable drill guide may only pivot in one plane.

11. The device according to claim 10, wherein the guide further comprises a clamping mechanism such that the at least two arms may be adjusted to exert pressure inwardly.

12. The device according to claim 10, wherein the pivotable drill guide is defined by a cylindrical wall defining a hollow having a diameter.

13. The device according to claim 12, wherein the auger drill bit further comprises a depth guide.

14. The device according to claim 13, wherein the depth guide of the auger drill bit comprises a shoulder having a diameter, the diameter of the shoulder being larger than the diameter of the pivotable drill guide.

15. A method for harvesting bone, the method including:
   disposing a guide along a bone, the guide having a drill guide pivotally connected thereto;
   inserting an auger drill bit into the drill guide;
   drilling into the bone at a first angle;
   removing the auger drill bit from the drill guide;
   pivoting the drill guide;
   inserting the auger drill bit into the drill guide; and
   drilling into the bone at a second angle.

16. The method for harvesting bone according to claim 15, wherein the auger drill bit has a distal end and a proximal end, the distal end including a helical cutting edge, and an elongate cylindrical hollow shaft; and
   wherein the guide includes a head portion with at least two arms configured to engage the iliac crest and a pivotable drill guide.

17. The method for harvesting bone according to claim 16, wherein the step of disposing a guide along a bone includes pressing the two arms of the guide down such that the two arms are positioned on the inside and outside of the iliac bone.

18. The method for harvesting bone according to claim 16, wherein the elongate cylindrical hollow shaft further includes a distal end and a proximal end, the proximal end having a void; and the method further comprises the step of collecting the drilled bone through the void.

19. The method according to claim 15, wherein the step of disposing a guide along a bone includes the step of clamping the guide in place on the bone.

* * * * *